United States Patent
Osaki et al.

(10) Patent No.: US 11,318,102 B2
(45) Date of Patent: May 3, 2022

(54) HARD CAPSULE SHOWING IMPROVED DEPOSITION OF GELLING ADJUVANT AND METHOD FOR PREPARATION THEREOF

(71) Applicant: QUALICAPS CO., LTD., Nara (JP)

(72) Inventors: Yoshiro Osaki, Nara (JP); Makoto Aso, Nara (JP)

(73) Assignee: QUALICAPS CO., LTD., Nara (JP)

( * ) Notice: Subject to any disclaimer, the term of this patent is extended or adjusted under 35 U.S.C. 154(b) by 0 days.

(21) Appl. No.: 16/465,009

(22) PCT Filed: Nov. 15, 2017

(86) PCT No.: PCT/JP2017/041048
§ 371 (c)(1),
(2) Date: May 29, 2019

(87) PCT Pub. No.: WO2018/105339
PCT Pub. Date: Jun. 14, 2018

(65) Prior Publication Data
US 2019/0282509 A1  Sep. 19, 2019

(30) Foreign Application Priority Data

Dec. 7, 2016 (JP) .............................. JP2016-237791

(51) Int. Cl.
| | |
|---|---|
| A61K 9/48 | (2006.01) |
| A23L 29/231 | (2016.01) |
| A23L 5/00 | (2016.01) |
| A61K 8/20 | (2006.01) |
| A61K 47/36 | (2006.01) |
| A61K 8/11 | (2006.01) |
| A61K 47/38 | (2006.01) |
| A23L 29/256 | (2016.01) |
| A61K 47/26 | (2006.01) |
| A61K 47/02 | (2006.01) |
| A61K 8/34 | (2006.01) |
| A61K 8/73 | (2006.01) |
| A23L 29/269 | (2016.01) |
| A61J 3/07 | (2006.01) |

(52) U.S. Cl.
CPC .............. *A61K 9/4816* (2013.01); *A23L 5/00* (2016.08); *A23L 29/231* (2016.08); *A23L 29/256* (2016.08); *A23L 29/269* (2016.08); *A61J 3/07* (2013.01); *A61K 8/11* (2013.01); *A61K 8/20* (2013.01); *A61K 8/34* (2013.01); *A61K 8/73* (2013.01); *A61K 9/48* (2013.01); *A61K 9/485* (2013.01); *A61K 9/4858* (2013.01); *A61K 9/4866* (2013.01); *A61K 47/02* (2013.01); *A61K 47/26* (2013.01); *A61K 47/36* (2013.01); *A61K 47/38* (2013.01); *A61K 9/4833* (2013.01)

(58) Field of Classification Search
None
See application file for complete search history.

(56) References Cited

U.S. PATENT DOCUMENTS

| | | | |
|---|---|---|---|
| 2,526,683 | A | 10/1950 | Murphy |
| 2,718,667 | A | 9/1955 | Malm et al. |
| 3,508,678 | A | 4/1970 | Graham et al. |
| 3,617,588 | A | 11/1971 | Langman |
| 3,823,843 | A | 7/1974 | Stephens et al. |
| 4,040,536 | A | 8/1977 | Schwarz |
| 4,069,819 | A | 1/1978 | Valentini et al. |
| 4,210,140 | A | 7/1980 | James et al. |
| 4,365,060 | A | 12/1982 | Onda et al. |
| 4,822,618 | A | 4/1989 | Schweiger et al. |
| 4,993,137 | A | 2/1991 | Muto et al. |
| 5,032,074 | A | 7/1991 | Muto et al. |
| 5,264,223 | A | 11/1993 | Yamamoto et al. |
| 5,431,917 | A | 7/1995 | Yamamoto et al. |
| 5,756,123 | A | 5/1998 | Yamamoto et al. |
| 5,769,267 | A | 6/1998 | Duynslager et al. |
| 6,499,279 | B1 | 12/2002 | Yamamoto et al. |
| 6,517,865 | B2 | 2/2003 | Cade et al. |
| 6,649,180 | B1 | 11/2003 | Matsuura et al. |
| 7,669,596 | B2 | 3/2010 | Alston |
| 8,365,296 | B2 | 1/2013 | Yasaki et al. |
| 9,138,920 | B2 | 9/2015 | De Bock et al. |
| 9,211,659 | B2 | 12/2015 | De Bock et al. |
| 2003/0072731 | A1* | 4/2003 | Gulian ................. A61K 9/2853 424/70.13 |
| 2007/0065501 | A1 | 3/2007 | He et al. |
| 2010/0024041 | A1 | 1/2010 | Yasaki et al. |
| 2010/0168410 | A1 | 7/2010 | Cade et al. |

(Continued)

FOREIGN PATENT DOCUMENTS

| | | |
|---|---|---|
| CN | 1927186 | 3/2007 |
| EP | 0714656 | * 6/1996 |

(Continued)

OTHER PUBLICATIONS

Extended European Search Report dated Jan. 9, 2020 in corresponding European Patent Application No. 17878539.0.
International Search Report dated Dec. 26, 2017 in International (PCT) Application No. PCT/JP2017/041048.
"Size-Exclusion Chromatography", Chromatography (621), The United States Pharmacopeia: USP30/The National Formulary/NF25, pp. 250-251.

*Primary Examiner* — Tigabu Kassa (74) *Attorney, Agent, or Firm* — Wenderoth, Lind & Ponack, L.L.P.

(57) ABSTRACT

An object of the present invention is to provide a hard capsule improved in deposition of a gelling aid on a hard capsule film. The gelling aid deposition is inhibited by adding a non-reducing disaccharide or a non-reducing disaccharide alcohol to the hard capsule film.

6 Claims, 1 Drawing Sheet

(56) References Cited

U.S. PATENT DOCUMENTS

2010/0233252 A1 9/2010 Tochio et al.
2010/0300440 A1 12/2010 Deboeck et al.

FOREIGN PATENT DOCUMENTS

| | | |
|---|---|---|
| JP | 3-279325 | 12/1991 |
| JP | 8-208458 | 8/1996 |
| JP | 2000-226097 | 8/2000 |
| JP | 2000-297102 | 10/2000 |
| JP | 2005-187412 | 7/2005 |
| JP | 2007-144014 | 6/2007 |
| JP | 2009-504630 | 2/2009 |
| JP | 2010-27003 | 2/2010 |
| JP | 2010-270039 | 12/2010 |
| WO | 2007/086586 | 8/2007 |

\* cited by examiner

HARD CAPSULE SHOWING IMPROVED DEPOSITION OF GELLING ADJUVANT AND METHOD FOR PREPARATION THEREOF

TECHNICAL FIELD

The present invention relates to a hard capsule improved in deposition of a gelling aid, a solution for preparing the hard capsule, and a method of preparing the hard capsule.

BACKGROUND ART

The method for producing hard capsules comprising a cellulose compound as a main component of a base includes thermal gelation methods and cold gelation methods. The cold gelation method can produce hard capsules by the same process as the hard capsule production using gelatin, thereby reducing device cost. Further, the cold gelation method is advantageous in terms of energy cost because the temperature at the time of drying can be as low as room temperature to about 40° C., and is also preferable in terms of environmental protection.

When a hard capsule comprising a cellulose compound as a main component of a capsule shell is famed by a cold gelation method, a gelling agent and a gelling aid (also referred to as "gelling promoter") are used. In particular, kappa-carrageenan used as a gelling agent and KCl used as a gelling aid exhibit high gelling performance at low temperatures, are excellent in terms of manufacturability (productivity) of hard capsules, and are effective for maintaining film hardness of hard capsules.

The high gelling performance at low temperature means that when a mold pin kept at around room temperature is immersed in a hard capsule-preparing solution and withdrawn therefrom, and the hard capsule-preparing solution is then cooled, the hard capsule-preparing solution exhibits a rapid and sharp viscosity increase with a decrease in temperature; and tends to gel more readily. If a hard capsule-preparing solution adhered to the mold pin surface is cured only by moisture evaporation, it takes several minutes to several tens of minutes to completely cure the capsule-preparing solution. During the curing time, the film material adhered to the pin drips, and thus fails to obtain a uniform capsule film. When the capsule-preparing solution has a high gelling performance, the solution is cured in a short period of time. Therefore, hard capsules of a uniform film thickness can be obtained. Furthermore, if a hard capsule film that is almost completely cured by gelation is then dried at an accelerated rate (for example, air of a higher temperature is blown during drying, or the amount of air is increased) to evaporate moisture from the film, the obtained hard capsule is less likely to have defects, such as wrinkles. High gelling performance also leads to shortening of the drying time, and can increase the number of hard capsules produced per unit time.

In general, the larger the amount of gelling agent added, the higher the gelling performance of the gelling agent. However, when a gelling agent is used in an excessively large amount, the capsule film is easily broken. Accordingly, in general, the amount of gelling agent added is typically 0.4 parts by mass, based on 100 parts by mass of hypromellose (Patent Literature (PTL) 1). The amount of gelling aid is increased as a larger amount of gelling agent is used. In general, the amount of gelling aid added is typically 0.6 parts by mass or less, based on 100 parts by mass of hypromellose (PTL 1).

To enhance the manufacturability of hard capsules, it is desirable to shorten the curing time as much as possible by improving gelling performance. One conceivable way to improve the gelling performance is, in addition to improving the gelling performance of the gelling agent itself, increasing the amount of gelling aid so as to promote gelation.

On the other hand, however, the addition of a large amount of gelling aid incurs a problem concerning deposition of the gelling aid due to its crystallization, particularly when the obtained hard capsule is stored under high humidity conditions. In particular, when the hard capsule is transparent, white powder adhesion is easily visually confirmed. Therefore, it is also undesirable in terms of external appearance and/or aesthetics.

It has been reported that such deposition can be inhibited by using hypromellose having a suitable degree of substitution; more specifically, by adding hypromellose having a degree of substitution of 2208 in an amount of 20 to 100%, based on 100% of the total hypromellose content in a hard capsule (Patent Literature (PTL) 2).

CITATION LIST

Patent Literature

PTL 1: JP2010-27003A
PTL 2: JP2000-297102A

SUMMARY OF INVENTION

Technical Problem

Although the method disclosed in PTL 2 has a gelling aid deposition inhibitory effect, it is difficult to enhance the productivity of hard capsules by further increasing the amount of gelling aid to be added.

An object of the present invention is to provide a hard capsule inhibited from deposition of a gelling aid, i.e., a hard capsule improved in deposition of a gelling aid, even when an increased amount of gelling aid is used.

Solution to Problem

The present inventors conducted extensive research, and found that the addition of a non-reducing disaccharide or a non-reducing disaccharide alcohol to a hard capsule film can provide a remarkable deposition inhibitory effect without impairing the advantageous properties of a hard capsule comprising a cellulose compound as a main component of a base, such as mechanical strength (hardness, cracking resistance) and dissolution. The present invention has been accomplished based on this finding, and includes the following embodiments.

I. Hard Capsule

I-1. A hard capsule comprising a film containing (1) a cellulose compound, (2) a gelling agent, (3) a gelling aid, and (4) at least one member selected from the group consisting of a non-reducing disaccharide and a non-reducing disaccharide alcohol, the film containing the gelling agent in an amount of 0.05 to 10 mass % and the gelling aid in an amount of more than 0.6 mass % and not more than 5 mass %, based on 100 mass % of the total film components of the hard capsule, excluding moisture.

I-2. The hard capsule according to Item I-1, wherein the film contains the at least one member selected from the group consisting of a non-reducing disaccharide and a non-reducing disaccharide alcohol in an amount of 1 to 10 mass %, based on 100 mass % of the total film components of the hard capsule, excluding moisture.

I-3. The hard capsule according to Item I-1 or I-2, wherein the cellulose compound is a water-soluble cellulose ether in which one or more hydrogen atoms of hydroxyl groups of cellulose are replaced with at least one group selected from the group consisting of alkyl and hydroxyalkyl.

I-4. The hard capsule according to any one of Items I-1 to I-3, wherein the cellulose compound is hydroxypropylmethylcellulose.

I-5. The hard capsule according to any one of Items I-1 to I-4, wherein the gelling agent is at least one member selected from the group consisting of carrageenan, pectin, and gellan gum.

I-6. The hard capsule according to any one of Items I-1 to I-5, wherein the gelling agent is kappa-carrageenan.

I-7. The hard capsule according to any one of Items I-1 to I-6, wherein the gelling aid is a compound capable of generating sodium ions, potassium ions, or calcium ions in an aqueous solution.

I-8. The hard capsule according to any one of Items I-1 to I-7, wherein the gelling aid is potassium chloride.

I-9. The hard capsule according to any one of Items I-1 to I-8, wherein the non-reducing disaccharide is at least one member selected from the group consisting of trehalose and sucrose.

I-10. The hard capsule according to any one of Items I-1 to I-9, wherein the non-reducing disaccharide alcohol is at least one member selected from the group consisting of maltitol, lactitol, and isomalt.

I-11. The hard capsule according to any one of Items I-1 to I-10, further comprising a plasticizer and/or a light-shielding agent.

II. Hard Capsule-Preparing Solution

II-1. A hard capsule-preparing solution containing (1) a cellulose compound, (2) a gelling agent, (3) a gelling aid, and (4) at least one member selected from the group consisting of a non-reducing disaccharide and a non-reducing disaccharide alcohol, the solution containing the gelling agent in an amount of 0.05 to 10 mass % and the gelling aid in an amount of more than 0.6 mass % and not more than 5 mass %, in the total film components, excluding solvent, based on 100 mass % of the total components of the solution, excluding solvent.

II-2. The hard capsule-preparing solution according to Item II-1, wherein the solution contains the at least one member selected from the group consisting of a non-reducing disaccharide and a non-reducing disaccharide alcohol in an amount of 1 to 10 mass %, in the total film components, excluding solvent, based on 100 mass % of the total components of the solution, excluding solvent.

II-3. The hard capsule-preparing solution according to Item II-1 or II-2, wherein the cellulose compound is a water-soluble cellulose ether in which one or more hydrogen atoms of hydroxyl groups of cellulose are replaced with at least one group selected from the group consisting of alkyl and hydroxyalkyl.

II-4. The hard capsule-preparing solution according to any one of Items II-1 to II-3, wherein the cellulose compound is hydroxypropylmethylcellulose.

II-5. The hard capsule-preparing solution according to any one of Items II-1 to II-4, wherein the gelling agent is at least one member selected from the group consisting of carrageenan, pectin, and gellan gum.

II-6. The hard capsule-preparing solution according to any one of Items II-1 to II-5, wherein the gelling agent is kappa-carrageenan.

II-7. The hard capsule-preparing solution according to any one of Items II-1 to II-6, wherein the gelling aid is a compound capable of generating sodium ions, potassium ions, or calcium ions in an aqueous solution.

II-8. The hard capsule-preparing solution according to any one of Items II-1 to II-7, wherein the gelling aid is potassium chloride.

II-9. The hard capsule-preparing solution according to any one of Items II-1 to II-8, wherein the non-reducing disaccharide is at least one member selected from the group consisting of trehalose and sucrose.

II-10. The hard capsule-preparing solution according to any one of Items I-1 to I-9, wherein the non-reducing disaccharide alcohol is at least one member selected from the group consisting of maltitol, lactitol, and isomalt.

II-11. The hard capsule-preparing solution according to any one of Items II-1 to II-10, further comprising a plasticizer and/or a light-shielding agent.

III. Method for Preparing Hard Capsule

III-1. A method for preparing a hard capsule comprising the step of preparing a hard capsule using the hard capsule-preparing solution according to any one of Items II-1 to II-11.

III-2. The method for preparing a hard capsule according to Item III-1, wherein the method is a cold gelation method.

III-3. The method for preparing a hard capsule according to Item III-1 or III-2, wherein the method is for inhibiting deposition of a gelling aid.

Advantageous Effects of Invention

According to the present invention, a hard capsule improved in tams of deposition of a gelling aid can be provided. The hard capsule has improved gelation performance, and further can be expected to enhance manufacturability (productivity) of hard capsules.

BRIEF DESCRIPTION OF DRAWINGS

FIG. 1 shows a film set in an Autograph tester. FIG. 1($a$) is a front view, and FIG. 1($b$) is a perspective view.

FIG. 2 shows a state in which a metal indenter compresses the film top. FIG. 2($a$) shows a state before compression, and FIG. 2($b$) shows a state after compression. FIG. 2($c$) shows a relationship between compression depth and compression test force. The indenter has a diameter of 9 mm.

DESCRIPTION OF EMBODIMENTS

1. Hard capsule

The hard capsule of the present invention comprises a film containing (1) a cellulose compound, (2) a gelling agent, (3) a gelling aid, and (4) at least one member selected from the group consisting of non-reducing disaccharides and non-reducing disaccharide alcohols.

In the present specification, "hard capsule" refers to a type of capsule that is produced by first producing a capsule film, and then encapsulating content in the capsule film produced. The capsule is usually composed of a cap portion and a body portion, and is also called a hard capsule or a two-piece capsule. The "hard capsule" of the present invention does not encompass soft capsules, which are produced by placing content between two sheets of film, and then adhering the two sheets of film to each other; seamless capsules, which are produced by dropwise adding content with a film solution to a solidification liquid; or microcapsules, which are prepared by incorporating an active ingredient inside via base material deposition or emulsification.

Examples of cellulose compounds that can be used in the present invention include water-soluble cellulose ethers in which one or more hydrogen atoms of hydroxyl groups of cellulose are replaced with at least one of alkyl groups or hydroxyalkyl groups. Examples of "alkyl groups" in the alkyl groups or hydroxyalkyl groups include linear or branched lower alkyl groups having 1 to 6 carbon atoms, and preferably 1 to 4 carbon atoms. Specific examples include methyl, ethyl, butyl, and propyl. Specific examples of water-soluble cellulose compounds include lower alkyl celluloses, such as methyl cellulose; hydroxy-lower alkyl celluloses, such as hydroxyethylcellulose and hydroxypropylcellulose; and hydroxy-lower alkyl alkyl celluloses, such as hydroxy-ethylmethylcellulose, hydroxyethylethylcellulose, and hydroxypropylmethylcellulose (herein sometimes also referred to as hypromellose or HPMC). Among these cellulose compounds, hydroxypropylmethylcellulose is the most preferable because of its excellent film-forming properties and mechanical strength under low-moisture conditions. The application of a cellulose compound to a hard capsule includes, for example, those disclosed in U.S. Pat. Nos. 2,526,683, 2,718,667, 3,617,588, 4,365,060, 4,993,137, 5,032,074, 5,431,917, 5,756,123, 6,517,865, 6,649,180, U.S. Pat. No. 2010/0168410, and U.S. Pat. Nos. 9,138,920, and 9,211,659. Examples of hydroxypropylmethylcellulose that can be used in the present invention include the hypromellose shown in Table 1, which is prescribed in the Japanese Pharmacopoeia.

TABLE 1

| Degree-of-substitution type | Methoxy group | Hydroxypropoxy group |
|---|---|---|
| 1828 | 16.5-20.0 | 23.0-32.0 |
| 2208 | 19.0-24.0 | 4.0-12.0 |
| 2906 | 27.0-30.0 | 4.0-7.5 |
| 2910 | 28.0-30.0 | 7.0-12.0 |

Examples of the hydroxypropylmethylcellulose of the present invention further include hypromellose of the following molecular weight, which has been approved for use as a food additive in Japan.
Molecular Weight
Unsubstituted structural units: 162.14
Substituted structural units: about 180 (degree of substitution: 1.19), about 210 (degree of substitution: 2.37) Polymer: about 13,000 (n=about 70) to about 200,000 (n=about 1000).

Commercially available hydroxypropylmethylcellulose typically has a weight average molecular weight (Mw)/number average molecular weight (Mn) (Mw/Mn) ratio within the range of 1.5 to 4. The weight average molecular weight (Mw) and the number average molecular weight (Mn) used to calculate this ratio (Mw/Mn) can both be determined by gel chromatography (size exclusion chromatography). The principle and method of the gel chromatography are not limited. For example, reference can be made to the description in the section "Size-Exclusion Chromatography" of the chapter "Chromatography" in "The United States Pharmacopeia: USP30/The National Formulary: NF25."

Examples of commercially available hydroxypropylmethylcellulose include the TC-5 series, the SB-4 (trademark) series, and the METOLOSE (trademark) series of Shin-Etsu Chemical Co., Ltd.; the AnyCoat-C (trademark) series of Lotte (formerly Samsung) Precision Chemistry Co. Ltd.; and the Methocel (trademark) series of The Dow Chemical Company. Further, the hypromellose that can be used in the present invention includes hypromellose having a viscosity of 3 to 50 mPa·s as measured at 20° C.±0.1° C. in the form of a 2 wt % aqueous solution of hypromellose.

In the present invention, hypromellose can be used singly, or in a combination of two or more. In any case, hypromellose having a "hypromellose viscosity value" within the range of 300 to 5000, preferably 300 to 1500, and more preferably 300 to 960 can be preferably used. The "hypromellose viscosity value" refers to the sum of products obtained by multiplying the viscosity of each hypromellose used to prepare a capsule film, as measured at 20° C.±0.1° C. in the form of a 2 wt % aqueous solution of hypromellose, by the proportion (parts by weight) of each hypromellose, based on 100 parts by weight of the total hypromellose amount. More specifically, when hypromellose having a viscosity of 6 mPa·s as measured in the form of a 2 wt % aqueous solution of hypromellose is used alone to produce a capsule film, the "hypromellose viscosity value" is 600, which is obtained by the following calculation: 6 mPa·s×100 parts by weight. When 30 parts by weight of hypromellose having a viscosity of 4 mPa·s and 70 parts by weight of hypromellose having a viscosity of 6 mPa·s, as measured in the form of a 2 wt % aqueous solution of hypromellose, are used in combination to produce a capsule film, the "hypromellose viscosity value" is 540, which is obtained by the following calculation: 4 mPa·s×30 parts by weight+6 mPa·s×70 parts by weight.

In general, a lower molecular weight leads to a lower viscosity. A low molecular weight, i.e., a low viscosity, provides better solubility of hard capsules; however, hard capsules with a low viscosity tend to be easily broken.

Accordingly, for oral pharmaceutical products in which good solubility is important, the viscosity is preferably 300 to 960. On the other hand, for inhalation drugs or foods in which breakage resistance is important, the viscosity is preferably 500 to 1500.

Examples of gelling agents include those that can be combined with a gelling agent, such as carrageenan, pectin, or gellan gum to gel the hard capsule-preparing solution. These can be used singly, or in a combination of two or more.

Among the above gelling agents, carrageenan has a high gel strength. Furthermore, carrageenan, even when used in a small amount, can provide an excellent gelation effect in the presence of specific ions. Therefore, carrageenan is the most preferable gelling agent. In general, three types of carrageenan are known: kappa-carrageenan, iota-carrageenan, and lambda-carrageenan. In the present invention, kappa-carrageenan and iota-carrageenan with relatively high hardness and gelation ability can be preferably used. Pectin can be classified into LM pectin and HM pectin, according to the difference in the degree of esterification. Gellan gum can also be classified into acylated gellan gum (native gellan gum) and deacylated gellan gum, according to the presence or absence of acylation. In the present invention, any of the above can be used, regardless of type.

The amount of gelling agent contained in the film of the hard capsule of the present invention is not limited, as long as the film of the hard capsule can be famed by the cold gelation method. The amount of gelling agent may be, for example, 0.05 to 10 mass %, preferably 0.1 to 9.5 mass %, more preferably 0.2 to 9 mass %, and even more preferably 0.3 to 8 mass %, based on 100 mass % of the total hard capsule film components, excluding moisture.

The gelling aid can also be selected according to the type of gelling agent used. The gelling aid has an effect of promoting gelation of the gelling agent, or may contribute to acceleration of the gelation by directly acting on the cellulose compound to raise or lower the gelation temperature or cloud point temperature. When carrageenan is used as a gelling agent, for example, the following gelling aids can be used in combination with carrageenan. For kappa-carrageenan, examples of usable gelling aids include compounds capable of generating one or more ions selected from sodium, potassium, ammonium, and calcium ions, such as potassium chloride, potassium phosphate, ammonium chloride, ammonium acetate, and calcium chloride. Preferred are compounds capable of generating sodium ions, potassium ions, or calcium ions in aqueous solutions. For iota-carrageenan, examples of usable gelling aids include compounds capable of generating calcium ions in water, such as calcium chloride. When gellan gum is used as a gelling agent, examples of gelling aids that can be used in combination with the gelling agent include compounds capable of generating in water one or more ions selected from sodium, potassium, calcium, and magnesium ions, such as sodium chloride, potassium chloride, calcium chloride, and magnesium sulfate. In addition, citric acid or sodium citrate can also be used as an organic acid or a water-soluble salt thereof.

The amount of gelling aid contained in the film of the hard capsule of the present invention can be set according to the amount of gelling agent. The amount of gelling aid can be in the range of at least more than 0.6 mass % to not more than 10 mass %, based on 100 mass % of the total hard capsule film components, excluding moisture. The lower limit of the amount of gelling aid is preferably 0.65 mass % or more, more preferably 0.7 mass % or more, even more preferably 1 mass % or more, and still even more preferably 2.6 mass % or more. The upper limit of the amount of gelling aid is preferably 5 mass % or less, more preferably 4 mass % or less, and still more preferably 3.5 mass % or less. The upper limit and the lower limit can be suitably combined.

When hydroxypropylmethylcellulose is used as a cellulose compound, the gelling agent used in combination with this cellulose compound is preferably, for example, carrageenan, and particularly preferably kappa-carrageenan; and the gelling aid used with this carrageenan is preferably, for example, potassium chloride.

In the present specification, the "disaccharide" means a sugar composed of two monosaccharides bonded together, such as sucrose, trehalose, maltose, lactose, turanose, and cellobiose. In the present invention, the disaccharide is preferably a non-reducing disaccharide. The presence or absence of reducibility depends on the presence or absence of an aldehyde group in the molecule. The non-reducing disaccharide is preferably at least one member selected from the group consisting of sucrose and trehalose. Sucrose and trehalose are both represented by the chemical formula $C_{12}H_{22}O_{11}$ and have non-reducing properties, which are exceptional for disaccharides.

As used herein, "disaccharide alcohol" includes sugar alcohols produced by reduction of carbonyl of aldose or ketose as a component of disaccharide. In the present invention, the disaccharide alcohol is preferably a non-reducing disaccharide alcohol. The non-reducing disaccharide alcohol is preferably at least one member selected from the group consisting of maltitol, lactitol, and isomalt. The reducibility of saccharides or sugar alcohols can be determined in aqueous solutions by the Fehling reaction disclosed in the "4.03 Digestion Test" of the "General Tests" in the 16th Japanese Pharmacopoeia. However, the reducibility of a sugar or sugar alcohol is derived from the reducibility of the aldehyde group contained in the chemical structure that can be formed in an aqueous solution.

The present inventors conducted extensive research on the effect of adding a carbohydrate, such as various monosaccharides, disaccharides, or disaccharide alcohols, to a capsule film mainly comprising a cellulose compound. As a result, the inventors found that non-reducing disaccharides and disaccharide alcohols can provide remarkable inhibitory effects on gelling aid deposition. In particular, non-reducing disaccharides were found to be more preferable, because the addition thereof provides a gelling aid deposition inhibitory effect with substantially no reduction in hardness of the capsule film.

The gelling aid deposition inhibitory effect achieved by using hypromellose of degree-of-substitution type 2208 as described in PTL 2 is not so high as the effect achieved by at least one carbohydrate selected from the group consisting of non-reducing disaccharides and non-reducing disaccharide alcohols. However, a combination of the hypromellose and at least one carbohydrate selected from the group consisting of non-reducing disaccharides and non-reducing disaccharide alcohols can provide a more remarkable inhibitory effect on gelling aid deposition.

The content of the at least one member selected from the group consisting of non-reducing disaccharides and non-reducing disaccharide alcohols in the hard capsule film is not limited, as long as deposition of the gelling aid can be inhibited. When at least two carbohydrates selected from the group consisting of non-reducing disaccharides and non-reducing disaccharide alcohols are used, the total amount of the carbohydrates is set within the range of amount described below. The content of the at least one member selected from the group consisting of non-reducing disaccharides and non-reducing disaccharide alcohols can be, for example, within the range of 1 mass % to 10 mass %, based on 100 mass % of the total hard capsule film components, excluding moisture. The lower limit of the content can be, for example, preferably 2 mass % or more, and more preferably 3 mass % or more. The upper limit of the content can be, for example, preferably 9 mass % or less, and more preferably 8 mass % or less. When the total amount of the at least one member selected from the group consisting of non-reducing disaccharides and non-reducing disaccharide alcohols exceeds 10% by mass, the hard capsule has reduced hardness. Therefore, it is preferable that the total amount does not exceed 10 mass %.

The hard capsule film of the present invention may comprise a plasticizer, a lubricant, a sequestrant, a colorant, a light-shielding agent, residual moisture (also simply referred to as moisture), etc., as components of the hard capsule film, if necessary.

Any plasticizer can be used without limitation, as long as it can be used for pharmaceutical products or food compositions. Examples of plasticizers include dioctyl adipate, adipic acid polyester, epoxidated soybean oil, diester of epoxyhexahydrophthalic acid, kaolin, triethyl citrate, glycerol, glycerol fatty acid ester, sesame oil, a mixture of dimethylpolysiloxane and silicon dioxide, D-sorbitol, medium-chain triglyceride, corn starch-derived liquid sugar alcohol, triacetin, concentrated glycerin, castor oil, phytosterol, diethyl phthalate, dioctyl phthalate, dibutyl phthalate, butyl phthalyl butyl glycolate, propylene glycol, polyoxyethylene (105) polyoxypropylene (5) glycol, Polysorbate 80, Macrogol 1500, Macrogol 400, Macrogol 4000, Macrogol 600, Macrogol 6000, isopropyl myristate, a mixture of cottonseed oil and soybean oil, glyceryl monostearate, isopropyl linoleate, and the like. When a plasticizer is used, the plasticizer can be usually added, for example, in an amount of 15 mass % or less, preferably 13 mass % or less, more preferably 11 mass % or less, and even more preferably 8 mass % or less, based on 100 mass % of the total hard capsule film components, excluding moisture.

Examples of sequestrants include ethylenediaminetetraacetic acid, acetic acid, boric acid, citric acid, gluconic acid, lactic acid, phosphoric acid, tartaric acid, or salts of these acids, metaphosphate, dihydroxyethylglycine, lecithin, β-cyclodextrin, and combinations thereof.

Any lubricant can be used without limitation, as long as it can be used for pharmaceutical products or food compositions. Examples of lubricants include calcium stearate, magnesium stearate, sodium stearyl fumarate, carnauba wax, starch, sucrose fatty acid ester, light anhydrous silicic acid, macrogol, talc, hydrogenated vegetable oil, and the like.

Any colorant and any light-shielding agent can be used without limitation, as long as they can be used for pharmaceutical products or food compositions. Examples of colorants include powdered gambir tannin, turmeric extract, methylrosanilinium chloride, yellow iron oxide, yellow iron sesquioxide, OPASPRAY K-1-24904, orange essence, brown iron oxide, carbon black, caramel, carmine, carotene liquid, β-carotene, light-sensitive element No. 201, licorice extract, gold leaf, *Sasa albomarginata* extract, black iron oxide, light anhydrous silicic acid, *Daemonorops draco* (kekketsu), zinc oxide, titanium oxide, iron sesquioxide, disazo yellow, Food Blue No. 1 and its aluminum lake, Food Blue No. 2 and its aluminum lake, Food Yellow No. 4 and its aluminum lake, Food Yellow No. 5 and its aluminum lake, Food Green No. 3 and its aluminum lake, Food Red No. 2 and its aluminum lake, Food Red No. 3 and its aluminum lake, Food Red No. 102 and its aluminum lake, Food Red No. 104 and its aluminum lake, Food Red No. 105 and its aluminum lake, Food Red No. 106 and its aluminum lake, sodium hydroxide, talc, sodium copper chlorophyllin, copper chlorophyll, powdered hull-less barley green tea extract, hull-less barley green tea extract, phenol red, sodium fluorescein, d-borneol, malachite green, octyldodecyl myristate, methylene blue, medicinal carbon, riboflavin butyrate, riboflavin, powdered green tea, manganese ammonium phosphate, riboflavin sodium phosphate, rose oil, turmeric color, chlorophyll, carminic acid color, Food Red No. 40 and its aluminum lake, water-soluble annatto, sodium iron chlorophyllin, dunaliella carotene, paprika color, carrot carotene, potassium norbixin, sodium norbixin, palm oil carotene, beat red, grape pericarp color, black currant color, monascus color, safflower red color, safflower yellow color, marigold color, sodium riboflavin phosphate, madder color, alkanet color, aluminum, potato carotene, shrimp color, krill color, orange color, cacao color, cacao carbon black, oyster color, crab color, carob color, fish scale foil, silver, kusagi (*Clerodendrum trichotomum*) color, gardenia blue color, gardenia red color, gardenia yellow color, kooroo color, chlorophin, kaoliang color, bone carbon black, bamboo grass color, Shea nut color, lithospermum root color, red sandalwood color, vegetable carbon black, sappan color, spirulina color, onion color, tamarind color, corn color, tomato color, peanut color, phaffia color, pecan nut color, monascus yellow, powdered annatto, haematococcus algae color, purple sweet potato color, purple corn color, purple yam color, vegetable oil soot color, lac color, rutin, enju (*Styphnolobium japonicum*) extract, buckwheat whole-plant extract, logwood color, red cabbage color, red rice color, red radish color, adzuki bean color, *Hydrangea serrata* leaf extract, sepia color, uguisukagura (*Lonicera gracilipes*) color, elderberry color, olive tea, cowberry color, gooseberry color, cranberry color, salmon berry color, strawberry color, dark sweet cherry color, cherry color, thimbleberry color, deberry color, pineapple juice, huckleberry color, grape juice color, black currant color, blackberry color, plum color, blueberry color, berry juice, boysenberry color, whortleberry color, mulberry color, morello cherry color, raspberry color, red currant color, lemon juice, loganberry color, chlorella powder, cocoa, saffron color, beefsteak plant color, chicory color, layer color, hibiscus color, malt extract, paprika powder, red beet juice, carrot juice, and the like.

Examples of light-shielding agents include titanium oxide, iron sesquioxide, yellow iron sesquioxide, black iron oxide, Food Blue No. 1 aluminium lake, Food Blue No. 2 aluminium lake, Food Yellow No. 4 aluminium lake, Food Yellow No. 5 aluminium lake, Food Green No. 3 aluminium lake, Food Red No. 2 aluminium lake, Food Red No. 3 aluminum lake, Food Red No. 102 aluminium lake, Food Red No. 104 aluminium lake, Food Red No. 105 aluminium lake, Food Red No. 106 aluminium lake, Red No. 40 aluminium lake, and the like. Pharmaceutical hard capsules may contain titanium oxide as a light-shielding agent to prevent degradation of content due to ultraviolet rays etc.

In general, the capsule film after preparation preferably contains a small percentage of residual moisture. When capsules after molding are dried at a temperature in the range of 30° C. to 100° C., the moisture content of the capsules settles to a specific saturated residual moisture level according to the solids content and the composition of the capsules. Naturally, when the drying treatment is performed at a higher temperature, the moisture content settles to a saturated moisture level in a shorter period of time. The residual moisture content depends on environmental humidity during capsule storage, and changes almost reversibly. That is, the saturated moisture level of the capsule film after fully drying at 30 to 100° C. settles to a constant value, if the film is further stored at a constant temperature and relative humidity for several days after the drying. In the present invention, the saturated moisture level after storage at room temperature and a relative humidity of 43% for several days is used.

Containing a small amount of residual moisture is rather preferable in order to maintain breakage resistance. The residual moisture content, as measured at room temperature and a relative humidity of 43% in terms of saturated moisture level, is preferably at least 1% or more, preferably 2% or more, and more preferably 3% or more, based on the total weight of the capsule film. On the other hand, an excessively large residual moisture content may cause a reaction with an encapsulated drug during long-term storage. Therefore, the residual moisture content is preferably 8% or less, and more preferably 6% or less.

The residual saturated moisture level can be expressed in terms of water content calculated from loss-on-drying, and can be measured in the following manner.

Method for Determining Water Content of Capsule Film by the Loss-On-Drying Method A sample (a hard capsule or a film) is placed into a desiccator having an atmosphere in which the humidity is made constant by placing a saturated aqueous solution of potassium carbonate in the desiccator, and the desiccator is sealed. The sample is moisture-controlled at 25° C. for 1 week. In the presence of a saturated aqueous solution of potassium carbonate, an atmosphere with a relative humidity of approximately 43% can be created. The weight (wet weight) of the sample after the moisture control is measured.

The sample is then heated at 105° C. for 2 hours, and the weight (dry weight) of the sample is measured again. From the difference between the weight of the sample before drying (wet weight) and the weight of the sample after drying (dry weight), the amount of water decreased by heating and drying at 105° C. for 2 hours (water content) is calculated according to the following formula.

Water content (%)=[(Wet weight of sample)−(Dry weight of sample)/Wet weight of sample]×100

2. Hard Capsule-Preparing Solution

The capsule-preparing solution for forming the hard capsule according to this embodiment comprises a solvent and film components described above in section 1. The solvent is not particularly limited, as long as it is an aqueous solvent. Examples of preferable solvents include water, ethanol, and a mixture thereof. Water is more preferable.

The amounts of film components contained in the hard capsule-preparing solution are not limited, as long as the film of the hard capsule can be formed by the cold gelation method. Based on 100 mass % of the total film components of the solution, excluding solvent, the amount of gelling agent in the total film components, excluding moisture, of the solution is 0.05 to 10 mass %, preferably 0.1 to 9.5 mass %, more preferably 0.2 to 9 mass %, and even more preferably 0.3 to 8 mass %.

The amount of gelling aid can be set according to the amount of gelling agent. Based on 100 mass % of the total film components of the hard capsule-preparing solution, excluding solvent, the amount of gelling aid contained in the total film components, excluding solvent, can be in the range of at least more than 0.6 mass % to not more than 10 mass %. The lower limit of the amount of gelling aid is preferably 0.65 mass % or more, more preferably 0.7 mass % or more, even more preferably 1 mass % or more, and still even more preferably 2.6 mass % or more. The upper limit of the amount of gelling aid is preferably 5 mass % or less, more preferably 4 mass % or less, and still more preferably 3.5 mass % or less. The upper limit and the lower limit can be suitably combined.

The content of the at least one member selected from the group consisting of non-reducing disaccharides and non-reducing disaccharide alcohols in the hard capsule-preparing solution is not limited, as long as deposition of the gelling aid can be inhibited. The content of the at least one member selected from the group consisting of non-reducing disaccharides and non-reducing disaccharide alcohols in the total film components, excluding solvent, can be in the range of 1 mass % to 10 mass %, based on 100% by mass of the total film components of the solution, excluding solvent. The lower limit of the content is preferably 2 mass % or more, and more preferably 3 mass % or more. The upper limit of the content is preferably 9 mass % or less, and more preferably 8 mass % or less.

When two or more carbohydrates selected from the group consisting of non-reducing disaccharides and non-reducing disaccharide alcohols are used, the total amount of the carbohydrates used should fall within the range of the content described above.

The final concentration in the capsule-preparing solution may be, for example, the following concentration. The final concentration refers to the concentration in the final solution, that is, the concentration in the solution actually used to prepare the capsule. The final concentration range of the total amount of the film components, excluding solvent, in the capsule-preparing solution may be, for example, in the range of 10 to 30 mass %, preferably 12 to 25 mass %, and more preferably 14 to 20 mass %.

The final concentration range of the cellulose compound, which is a main component, may be, for example, 10 to 30 mass %, preferably 12 to 25 mass %, and more preferably 14 to 20 mass %. The final concentration of the gelling agent may be, for example, 0.005 to 0.5 mass %, preferably 0.01 to 0.45 mass %, and more preferably 0.015 to 0.4 mass %. The final concentration of the gelling aid may be, for example, 0.06 to 3% by mass. The lower limit of the amount of gelling aid is preferably 0.07 mass % or more, more preferably 0.1 mass % or more. The upper limit of the amount of gelling aid is preferably 1.8 mass % or less, more preferably 1.5 mass % or less, and still more preferably 1.2 mass % or less. The upper limit and the lower limit can be suitably combined.

The final concentration of the at least one member selected from the group consisting of non-reducing disaccharides and non-reducing disaccharide alcohols can be within the range of 0.03 to 2.5 mass %. The lower limit of the content is preferably 0.1 mass % or more, and more preferably 0.2 mass % or more. The upper limit of the content is preferably 3.5 mass % or less, more preferably 3 mass % or less, and still more preferably 2.5 mass % or less. When the capsule-preparing solution contains a lubricant, a colorant, a light-shielding agent, a sequestrant, a flavoring agent, and the like, the amount of each of such additives can be set within the range of 0.5 mass % or less.

3. Method for Preparing Hard Capsule

The method for preparing the capsule-preparing solution (immersion liquid) is not particularly limited. Examples of methods include, but are not limited to, a method in which after a gelling agent, a gelling aid, a non-reducing disaccharide, and a non-reducing disaccharide alcohol are dispersed and/or dissolved in purified water heated to about 70 to 80° C., a water-soluble cellulose compound is dispersed in the purified water, and the dispersion is then cooled to a desired temperature of immersion liquid (usually 35 to 60° C., preferably 40 to 60° C.) to dissolve the water-soluble cellulose compound, thus preparing a uniform capsule-preparing solution (immersion liquid); and a method in which after a water-soluble cellulose compound is dispersed in hot water of about 70 to 90° C. and the dispersion is once cooled to dissolve the water-soluble cellulose compound, the resulting solution is heated again to about 30 to 60° C., and a gelling agent and a gelling aid are added to and dissolved in the solution to prepare a uniform capsule-preparing solution (immersion liquid), followed by adjusting the solution to a desired temperature of immersion liquid. The viscosity of the capsule-preparing solution is not particularly limited. Preferably, the viscosity of the capsule-preparing solution can be adjusted to 100 to 20,000 mPa·s, and more preferably 300 to 10,000 mPa·s, under the temperature conditions used for immersion of a capsule-forming pin (temperature of immersion liquid) (30 to 80° C., preferably 40 to 60° C.). The solvent content of the capsule-preparing solution may be, for example, typically 60 to 90 mass %, and preferably 70 to 85 mass %.

The viscosity herein refers to a viscosity as measured with a Brookfield rotational viscometer at a predetermined temperature at 60 rpm for 1 minute using a No. 2 rotor for a viscosity of less than 500 mPa·s, a No. 3 rotor for a viscosity of at least 500 mPa·s and less than 2000 mPa·s, and a No. 4 rotor for a viscosity of 2000 mPa·s or more. The concentration of each component contained in the capsule-preparing solution is described below.

The method for preparing (molding) a hard capsule is not particularly limited, as long as the capsule-preparing solution according to the present invention is used to prepare a capsule. A hard capsule is generally produced by immersing a mold pin, which is a mold for forming capsules, into an aqueous solution of capsule film-forming components; then curing and drying the film adhering to the mold pin when the mold pin is withdrawn from the solution, to thereby obtain a capsule with a desired shape and thickness (the dipping method). Specifically, the method for preparing a hard capsule may comprise the steps of: preparing a capsule-preparing solution, for example, by producing a capsule-preparing solution by the above method, or purchasing a capsule-preparing solution; and dipping a capsule-forming pin into the capsule-preparing solution and then withdrawing the pin from the solution to allow the solution adhering to the capsule-forming pin to gel, followed by drying the gelled film at 20 to 80° C. to prepare a capsule. More specifically, the hard capsule used in the present invention can be produced through the following molding steps:

(1) a step of immersing a capsule-forming pin into a capsule-preparing solution (immersion liquid) containing a cellulose compound, a gelling agent, a gelling aid, and at least one member selected from non-reducing disaccharides and non-reducing disaccharide alcohols (dipping step);
(2) a step of withdrawing the capsule-forming pin from the capsule-preparing solution (immersion liquid) to allow the solution adhering to the outer surface of the capsule-forming pin to gel (gelation step);
(3) a step of drying the gelled capsule film (gelled film) formed on the outer surface of the capsule-forming pin (drying step); and
(4) a step of removing the dried capsule film from the capsule-forming pin (removal step).

If necessary, the following heating step may be performed after step (4):
(5) a step of heating the gelled capsule film (gelled film) to 30 to 150° C., which is performed after the gelation step (2) and which may be before, after, or simultaneously with the drying step (3) or after the removal step (4).

When a solution containing kappa-carrageenan as a gelling agent is used as a capsule-preparing solution (immersion liquid), the gelation step (2) can be performed by adjusting the surrounding temperature of the capsule manufacturing machine to typically 35° C. or less, preferably 30° C. or less, and more preferably room temperature or lower, so as to allow the capsule-preparing solution adhering to the outer surface of the capsule-forming pin to cool (cold gelation method), which relies on the fact that the gelling agent becomes a gel at a temperature of about 40° C. or less. Specifically, in the dipping step (1), a capsule-forming pin, which is adjusted to an appropriate temperature of 10 to 30° C., preferably 13 to 28° C., and more preferably 15 to 25° C., according to the liquid temperature of a capsule-preparing solution (immersion liquid), is immersed in the capsule-preparing solution, which is kept at a constant temperature of 35 to 60° C., preferably 40 to 60° C. Subsequently, in the gelation step (2), the capsule-forming pin is withdrawn from the capsule-preparing solution (immersion liquid) to allow the capsule-preparing solution adhering to the outer surface of the capsule-forming pin to gel.

The drying step (3) can be performed at room temperature. The drying step (3) is usually performed by blowing room-temperature air. The removal step (4) is performed by detaching, from the capsule-forming pin, the dry capsule film formed on the surface of the capsule-molding pin.

The optional heating step (5) can be performed after the gelation step (2), that is, after the capsule-preparing solution becomes a gel (is solidified). The heating treatment may be performed at any stage after the gelation step (2); and can be performed, for example, before, after, or simultaneously with the drying step (3), or after the removal step (4). Preferably, after the gelation step (2), the gelled capsule film is subjected to a drying step at room temperature, and a heating treatment is performed with the gelled capsule film being in a dried or semi-dried state. The heating treatment can be usually performed by sending air of 20 to 50° C. The heating temperature is not particularly limited, as long as it is within the range of 20 to 150° C. The heating temperature is preferably in the range of 25 to 80° C., and more preferably 30 to 50° C.

The capsule film thus prepared is cut to a predetermined length, and then provided as a hard capsule with a pair of a body portion and a cap portion being engaged or not engaged with each other.

The film thickness of hard capsules is usually in the range of 50 to 200 μm. In particular, the side-wall thickness of currently commercially available capsules is typically 70 to 150 μm, and preferably 80 to 120 μm. The size of hard capsules includes Size No. 00, No. 0, No. 1, No. 2, No. 3, No. 4, No. 5, etc. In the present invention, any size of hard capsules can be used.

Further, the method for preparing a hard capsule is also a method for inhibiting deposition of a gelling aid on the hard capsule after preparation.

4. Filling of Hard Capsule with Content, and Use of the Hard Capsule

The method of filling the hard capsule with content is not particularly limited.

Filling of the hard capsule with content can be performed, for example, by using a known capsule-filling machine, such as a fully automatic capsule-filling machine (model name: LIQFIL super 80/150, produced by Qualicaps Co., Ltd.) or a capsule-filing and sealing machine (model name: LIQFIL super FS, produced by Qualicaps Co., Ltd.), as disclosed, for example, in JP2007-144014A or JP2000-226097A.

In the filling method, provisional joining and true joining of hard capsules are secured by a lock mechanism as disclosed in U.S. Pat. Nos. 3,508,678, 3,823,843, 4,040,536, 4,822,618, 5,769,267, etc. The hardness of the hard capsule is also important to stably maintain such a lock mechanism.

In order to prevent malicious opening and foreign-matter entry, and to securely prevent leaks of liquid filling materials by more secure sealing in addition to the above-described lock mechanism by rubbing the cap and the body together, the capsule fitting portion may be sealed by using the band seal disclosed in JP2005-187412A or JP2009-504630A. The use of the hard capsule of the present invention is not particularly limited. Preferable examples of uses include oral preparations, inhalation preparations, and the like.

Preferably, oral preparations are promptly dissolved in the stomach or intestines. In order to allow a capsule film to be dissolved in the intestines and release a pharmaceutical agent in the intestines, enteric capsules can also be formed by the capsule film surface with an enteric base material. Enteric capsules can also be famed by making a capsule film itself exclusively or partially using an enteric base material. The enteric capsule is not particularly limited as long as it has a property of not being dissolved in the stomach, but being dissolved in the intestines. For example, the enteric capsules may be capsules that are hardly dissolved in a dilute hydrochloric acid solution of pH 1.2 (Japanese Pharmacopoeia, first fluid) for more than 2 hours, and that are dissolved in a buffer solution of pH 6.8 (Japanese Pharmacopoeia, second fluid).

Further, a drug can be released from the hard capsule in a sustained manner. For gradual sustained release of a drug, the capsule film surface may be coated with a sustained-release film.

Inhalation preparations can be produced by sealing a single dose of a drug in each hard capsule and placing the capsule in a device, as disclosed in, for example, U.S. Pat. Nos. 4,069,819, 4,210,140, 7,669,596, or U.S. Pat. No. 2010-0300440A. The capsule is pierced with a small pin, or broken to enable inhalation of the drug inside at an appropriate flow rate.

The content encapsulated in the hard capsule is not particularly limited. Examples include, but are not limited to, pharmaceutical products for humans and animals, quasi-drugs, cosmetics, and foods. The form of the content is also not particularly limited. For example, the content may be in the form of a liquid, gel, powder, granules, tablets, pellets, or a mixture thereof (a hybridized state).

When the content encapsulated in the hard capsule is a pharmaceutical product, examples of the pharmaceutical product include at least one kind of pharmaceutical ingredient selected from nourishment tonics, antipyretic/analgesic/anti-inflammatory drugs, psychotropic drugs, anti-anxiety drugs, antidepressant drugs, hypnotic/sedative drugs, antispasmodic drugs, drugs acting on the central nervous system, cerebral metabolism improvers, cerebral circulation improvers, antiepileptic drugs, sympathetic nerve stimulants, digestives, antacids, antiulcer drugs, antitussive/expectorant drugs, antiemetic drugs, respiration promoters, bronchodilators, antiallergic drugs, drugs for dentistry and oral cavity, antihistaminic drugs, cardiotonic drugs, antiarrhythmic drugs, diuretic drugs, antihypertensive drugs, vasoconstrictors, coronary vasodilators, peripheral vasodilators, antihyperlipidemic drugs, cholagogues, antibiotics, chemotherapeutic drugs, antidiabetic drugs, antiosteoporotic drugs, antirheumatic drugs, skeletal muscle relaxants, spasmolytic drugs, hormone preparations, alkaloid narcotics, sulfa drugs, anti-gout drugs, anticoagulant drugs, antineoplastic drugs, and the like. Such pharmaceutical ingredients are not particularly limited, and can be selected, for example, from a wide variety of known pharmaceutical ingredients. Specific examples include the ingredients described in paragraphs [0055] to [0060] of WO2006/070578.

When the content encapsulated in the hard capsule is a food, examples include, but are not limited to, functional ingredients, such as docosahexaenoic acid, eicosapentaenoic acid, α-lipoic acid, royal jelly, isoflavone, agaricus, acerola, aloe, aloe vera, turmeric, L-carnitine, oligosaccharide, cacao, catechin, capsaicin, chamomile, agar, tocopherol, linolenic acid, xylitol, chitosan, GABA, citric acid, chlorella, glucosamine, ginseng, coenzyme Q10, brown sugar, collagen, chondroitin, bracket fungus, squalene, stevia, ceramide, taurine, saponin, lecithin, dextrin, *Houttuynia cordata*, niacin, *Bacillus natto*, bittern, lactic acid bacteria, saw palmetto, honey, *Coix lacryma-jobi* var. *ma-yuen*, Japanese apricot (ume) extract, pantothenic acid, hyaluronic acid, vitamin A, vitamin K, vitamin C, vitamin D, vitamin B1, vitamin B2, vitamin B6, vitamin B12, quercetin, protein, propolis, mulukhiya, folic acid, lycopene, linoleic acid, rutin, and *Ganoderma lucidum*.

5. Evaluation of Deposition of Gelling Aid

The deposition of the gelling aid on the hard capsule film is evaluated, for example, by preparing the capsule-preparing solution described above; then forming a film using a cast film applicator, and evaluating deposition of the gelling aid on the film. The obtained film has a thickness of 100 µm±5 µm. The film is cut into a size of 10 mm×50 mm, and then allowed to stand under the conditions of 25° C. and a relative humidity of 60% (in the presence of a saturated aqueous ammonium nitrate solution) for one week. The deposition of the gelling aid can be evaluated by visually checking whether the film becomes turbid. When no turbidity is visually observed, the capsule film can be evaluated as having "no deposition."

6. Evaluation of Hardness

The hardness of the hard capsule can be evaluated, for example, by preparing the capsule-preparing solution described above, then forming a film using a cast-film applicator, and evaluating hardness of the film. The obtained film has a thickness of 100 µm±5 µm. The film is cut into a size of 10 mm×50 mm, and then moisture-controlled at 25° C. and a relative humidity of 43% (a saturated aqueous solution of potassium carbonate), for example, for 1 week, and the hardness of the film is then evaluated in a compression test.

Figures 1A, 1B:
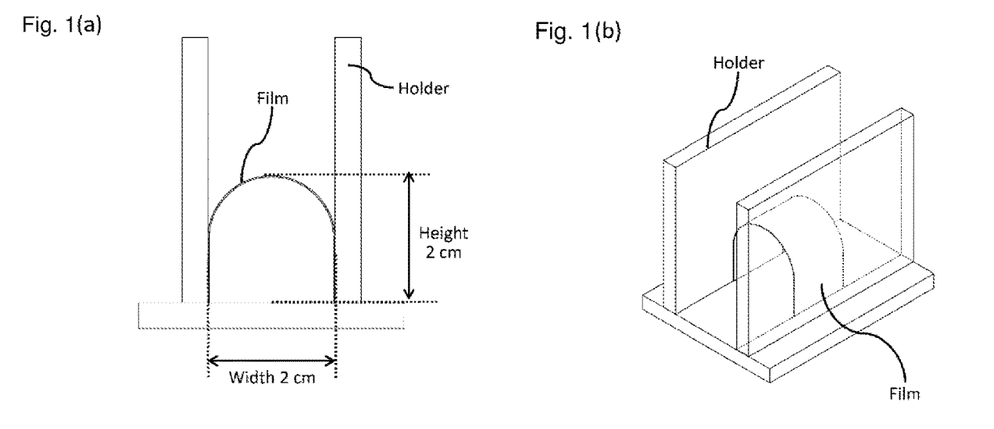
Figures 2A, 2B, 2C:
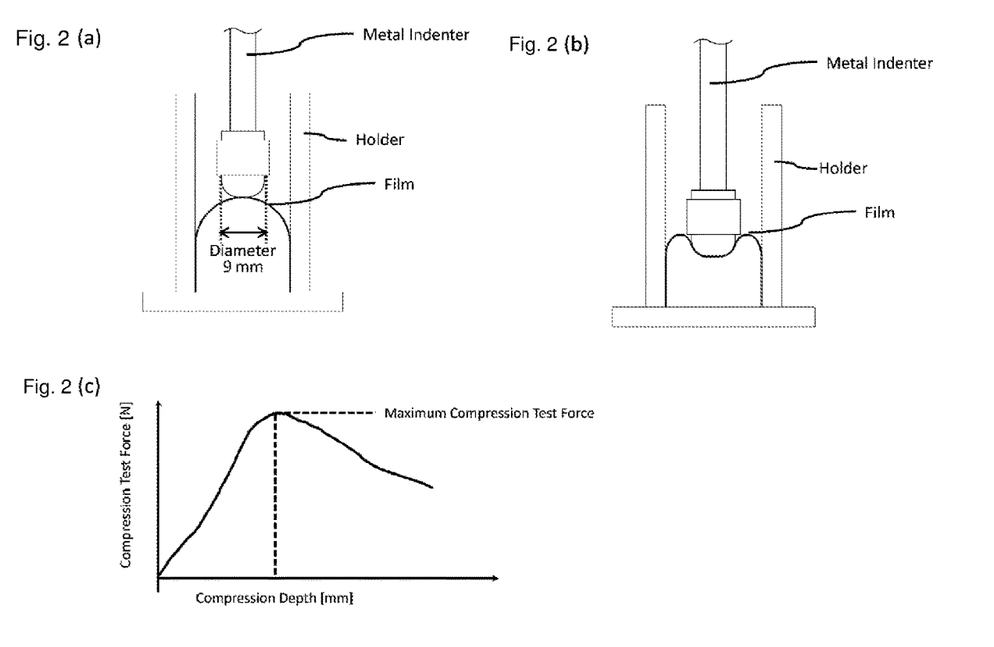

The hardness is evaluated in the following manner. The moisture-controlled film curved into an arch shape is set in the holder of an autograph tester (for example, AGS-J: Shimadzu Corporation) (as shown in FIG. 1a, the film set in the holder had a width of 2 cm and a height of 2 cm). A 5- to 8-mm film top is compressed with a metal indenter (FIG. 2b), and the peak of the compression test force value of the film is determined (FIG. 2c). The obtained value is compared with the value of the compression test force of a reference standard (a film produced using the same components as those of the test specimen, except for the carbohydrate; and containing the base in an amount increased by an amount corresponding to the amount of carbohydrate), thereby evaluating the hardness. The compression speed is, for example, 50 mm/min, and the diameter of the metallic indenter is, for example, 9 mm (FIG. 2b).

The hardness can be evaluated, for example, according to the following criteria, with the compression test force of the carbohydrate-free standard reference described below being defined as 100. A compression test force of 90 can be assessed as "unchanged hardness." A compression test force of less than 90 can be assessed as "weakening."

EXAMPLES

The present invention is described below more specifically with reference to Examples. However, the present invention is not limited to the Examples.

1. Preparation of Capsule Film

When deposition of a gelling aid on a hard capsule film and hardness of a hard capsule are evaluated, the measurement values change depending on the capsule film thickness, in particular, the film thickness of the capsule body portion compressed by a metal indenter. In particular, in the hardness evaluation, it is important to make a comparison using film samples having an identical thickness. Therefore, the deposition of a gelling aid and the hardness, which depend on the kinds and amounts of hard capsule components, were evaluated by producing, instead of hard capsules formed by a dipping method, films having the same compositions as those of the hard capsules by a casting method, for each composition of the hard capsule; and evaluating these films. In the following Examples, the evaluation was performed by producing, instead of hard capsules formed by a dipping method, films having the same compositions as those of the hard capsules. The films have excellent uniformity in thickness and excellent reproducibility in the evaluation, thus desirably reflecting inhibitory effects on gelling aid deposition and hardness of the capsule film.

1-1. Preparation of Capsule-Preparing Solution

As shown in Table 2, the HPMC used as a base in the following Examples is a mixture of two or three kinds of HPMC of degree-of-substitution type 2910 having different molecular weights. It has been confirmed that the gelling aid deposition and capsule film hardness do not depend on the hypromellose viscosity value. The hypromellose products of a degree-of-substitution type 2910 used in the experiments were AW4 and AW6, which are AnyCoat-C series with viscosity grades 4 and 6 produced by Samsung (currently known as Lotte); and TC-5R, which is a TC-5 series with viscosity grade 6 produced by Shin-Etsu Chemical Co., Ltd. When the viscosity grade (viscosity value) level was the same, no influence due to the difference in hypromellose manufacturer was observed in the gelling aid deposition or hardness.

The concentration of the film components of the hard capsule, excluding solvent, in the capsule-preparing solution was appropriately adjusted within the range of 10 to 25 mass %, in order to obtain a cast film of a desired thickness. Tables 2 and 3 show the amount of each component, based on 100 mass % of the total capsule film components, excluding moisture.

Kappa-carrageenan, and sodium chloride or potassium chloride as a gelling aid, were added to purified water and dispersed by stirring, and heated to 80° C. After dissolution of the materials was confirmed, at least one member selected from the group consisting of non-reducing disaccharides and non-reducing disaccharide alcohols was dissolved. Thereafter, while the liquid temperature was kept at 80° C., HPMC was added and dispersed, and the dispersion was allowed to stand for 30 minutes. Air bubbles were removed by vacuum deaeration. Subsequently, while stirring with a three-one motor, the dispersion was cooled to 50° C. to 60° C. and stirred with the three-one motor for 1 hour, thereby preparing a jelly-like capsule-preparing solution.

TABLE 2

| Composition | | | | Ref. Ex. 1 | Ref. Ex. 2 | Comp. Ex. 1 | Comp. Ex. 2 | Ex. 1 | Ex. 2 | Ex. 3 | Ex. 4 | Ex. 5 | Comp. Ex. 3 |
|---|---|---|---|---|---|---|---|---|---|---|---|---|---|
| κ-Carrageenan (mass %) | | | | 1.5 | 1.5 | 1.5 | 1.5 | 1.5 | 1.5 | 1.5 | 1.5 | 1.5 | 1.5 |
| Potassium chloride (mass %) | | | | 0.5 | 0.8 | 0.8 | 0.8 | 0.7 | 0.8 | 0.8 | 0.8 | 0.8 | 0.8 |
| | Sugar added | Product name | Manufacture name | | | | | | | | | | |
| Mono-saccharide | Glucose | D(+)-Glucose | Merck | | | 8 | | | | | | | |
| Disaccharide | Fructose | D(−)-Fructose | Wako Pure Chemical Industries, Ltd. | | | | 8 | | | | | | |
| | Trehalose | Trehalose 100 PH | Hayashibara Co., Ltd. | | | | | | 3 | 5 | | 8 | |
| | Sucrose | Purified white sugar | Wako Pure Chemical Industries, Ltd. | | | | | | | | 5 | | 8 |
| | Lactose | Pharmatose 100M | DFE Pharma | | | | | | | | | | 8 |
| | Maltose | Maltose monohydrate | Merck | | | | | | | | | | |
| | Sucralose | Sucralose P | B Food Science Co., Ltd. | | | | | | | | | | |
| Sugar alcohol | Maltitol | SweetPearl P200 | Roquette | | | | | | | | | | |
| | Lactitol | Lactitol LC-0 | B Food Science Co., Ltd. | | | | | | | | | | |
| | Xylitol | XYLISORB 700 | Roquette | | | | | | | | | | |
| | Mannitol | PEARLITOL 50C | Roquette | | | | | | | | | | |
| | Erythritol | Erythritol T | Mitsubishi-Chemical Foods Corporation | | | | | | | | | | |
| | Sorbitol | NEOSORB P 20/60 | Roquette | | | | | | | | | | |
| | Isomalt | galenIQ 800 | Beneo | | | | | | | | | | |
| Hardness | | | | 100 | 103 | 87 | 89 | 103 | 103 | 102 | 98 | 101 | 111 |
| Day on which KCL deposition was confirmed (up to 1 week) | | | | ○ | After 1 day | After 1 day | After 1 day | ○ | ○ | ○ | ○ | ○ | After 2 days |

| Composition | | | | Comp. Ex. 4 | Comp. Ex. 5 | Ex. 6 | Ex. 7 | Ex. 8 | Comp. Ex. 6 | Comp. Ex. 7 | Comp. Ex. 8 | Comp. Ex. 9 | Ex. 9 |
|---|---|---|---|---|---|---|---|---|---|---|---|---|---|
| κ-Carrageenan (mass %) | | | | 1.5 | 1.5 | 1.5 | 1.5 | 1.5 | 1.5 | 1.5 | 1.5 | 1.5 | 1.5 |
| Potassium chloride (mass %) | | | | 0.8 | 0.8 | 0.7 | 0.8 | 0.8 | 0.8 | 0.8 | 0.8 | 0.8 | 0.8 |
| | Sugar added | Product name | Manufacture name | | | | | | | | | | |
| Mono-saccharide | Glucose | D(+)-Glucose | Merck | | | | | | | | | | |
| Disaccharide | Fructose | D(−)-Fructose | Wako Pure Chemical Industries, Ltd. | | | | | | | | | | |

TABLE 2-continued

Table 2

| | | Product name | Manufacture name | | | | | | | | | | |
|---|---|---|---|---|---|---|---|---|---|---|---|---|---|
| | Trehalose | Trehalose100 PH | Hayashibara Co., Ltd. | | | | | | | | | | |
| | Sucrose | Purified white sugar | Wako Pure Chemical Industries, Ltd. | | | | | | | | | | |
| | Lactose | Pharmatose 100M | DFE Pharma | | | | | | | | | | |
| | Maltose | Maltose monohydrate | Merck | 8 | | | | | | | | | |
| | Sucralose | Sucralose P | B Food Science Co., Ltd. | | 8 | | | | | | | | |
| Sugar alcohol | Maltitol | SweetPearl P200 | Roquette | | | 3 | 8 | | | | | | |
| | Lactitol | Lactitol LC-0 | B Food Science Co., Ltd. | | | | | 8 | | | | | |
| | Xylitol | XYLISORB 700 | Roquette | | | | | | 8 | | | | |
| | Mannitol | PEARLITOL 50C | Roquette | | | | | | | 8 | | | |
| | Erythritol | Erythritol T | Mitsubishi-Chemical Foods Corporation | | | | | | | | 8 | | |
| | Sorbitol | NEOSORB P 20/60 | Roquette | | | | | | | | | 8 | |
| | Isomalt | galenIQ 800 | Beneo | | | | | | | | | | 8 |
| Hardness | | | | 109 | 115 | 106 | 101 | 103 | 82 | 82 | 94 | 94 | 104 |
| Day on which KCL deposition was confirmed (up to 1 week) | | | | After 1 day | After 5 days | ○ | ○ | ○ | After 1 day | After 1 day | After 1 day | After 1 day | ○ |

TABLE 3

| Composition | | | | Ref. Ex. 3 | Ex. 10 | Comp. Ex. 10 |
|---|---|---|---|---|---|---|
| κ-Carrageenan (mass %) | | | | 1.5 | 1.5 | 1.5 |
| Sodium chloride (mass %) | | | | 0.8 | 0.8 | 0.8 |

| | Sugar added | Product name | Manufacture name | | | |
|---|---|---|---|---|---|---|
| Monosaccharide | Glucose | D(+)-Glucose | Merck | | | |
| Disaccharide | Fructose | D(−)-Fructose | Wako Pure Chemical Industries, Ltd. | | | |
| | Trehalose | Trehalose100 PH | Hayashibara Co., Ltd. | | 8 | |
| | Sucrose | Purified white sugar | Wako Pure Chemical Industries, Ltd. | | | |
| | Lactose | Pharmatose 100M | DFE Pharma | | | |
| | Maltose | Maltose monohydrate | Merck | | | |
| | Sucralose | Sucralose P | B Food Science Co., Ltd. | | | |
| Sugar alcohol | Maltitol | SweetPearl P200 | Roquette | | | |
| | Lactitol | Lactitol LC-0 | B Food Science Co., Ltd. | | | |
| | Xylitol | XYLISORB 700 | Roquette | | | |
| | Mannitol | PEARLITOL 50C | Roquette | | | |
| | Erythritol | Erythritol T | Mitsubishi-Chemical Foods Corporation | | | 8 |
| | Sorbitol | NEOSORB P 20/60 | Roquette | | | |
| | Isomalt | galenIQ 800 | Beneo | | | |
| Hardness | | | | 100 | 103 | 81 |
| Day on which NaCl deposition was confirmed (up to 1 week) | | | | After 5 days | ○ | After 2 days |

1-2. Method for Forming Film

To obtain a casted-film, a metallic applicator was set on a glass surface or a PET film kept at room temperature. A capsule-preparing solution of 50° C. to 60° C. was poured and moved at a constant speed, thereby producing a uniform film. To ensure a uniform film thickness of 100 μm, an applicator having a gap of 0.4 mm to 1.5 mm was used as necessary. The film was then dried at room temperature to 30° C. for about 10 hours.

2. Evaluation of Deposition of Gelling Aid

After the obtained film was cut into a size of 10 mm×50 mm, the film was allowed to stand under the conditions of 25° C. and a relative humidity of 60% (in the presence of a saturated aqueous solution of ammonium nitrate) for 1 week. The deposition of the gelling aid was evaluated by visually checking for whether the film became turbid.

When no turbidity was visually observed, the capsule film can be evaluated as having "no deposition" of the gelling aid.

3. Evaluation of Hardness

The prepared film was cut into 10 mm×50 mm strips, and then moisture-controlled at 25° C. and a relative humidity of 43% (a saturated aqueous solution of potassium carbonate) for one week. After the moisture control, the hardness was evaluated by a compression test.

The hardness was evaluated by setting the moisture-controlled film curved into an arch shape in the holder of an Autograph tester (AGS-J: Shimadzu Corporation) (as shown in FIG. 1a, the film set in the holder had a width of 2 cm and a height of 2 cm). A 5- to 8-mm film top was compressed with a metal indenter (FIG. 2b), and the peak of the compression test force of the film was determined (FIG. 2c). The compression speed is, for example, 50 mm/min, and the diameter of the metallic indenter is 9 mm (FIG. 2b). The state of applying the compression test force to the body portion of a hard capsule was thus simulatively reproduced.

The measured compressive stress of each film was compared with the value of compression test force of a reference standard (a film produced using the same components as those of the test specimen, except for a hardness improving agent; and containing the base in an amount increased by an amount corresponding to the amount of the hardness improving agent), thereby evaluating the hardness. The relative compressive stress was evaluated with the compression test force of the reference standard being assumed as 100.

4. Results

Tables 2 and 3 show the compositions of the obtained films, as well as evaluation results of gelling aid deposition inhibitory effect and hardness. In Tables 2 and 3, "o" indicates that no deposition of the gelling aid was observed even 1 week after the film preparation. The composition of Reference Example 1 shown in Table 2 comprises potassium chloride as a gelling aid whose content is at the same level as the gelling aid content of conventional hard capsule film. Since no deposition of the gelling aid was observed in Reference Example 1, the results show that when the potassium chloride content is at the same level as the conventional gelling aid content, problematic deposition of the gelling aid does not occur after preparing capsules. As shown in the results of Reference Example 2 in Table 2, when the amount of potassium chloride used as a gelling aid was increased to 0.8 mass %, potassium chloride deposited. This tendency was also observed in Reference Example 3, in which sodium chloride was added in an amount of 0.8 mass %; 5 days after the film preparation, deposition of sodium chloride was observed.

On the other hand, gelling aid deposition inhibitory effects of various monosaccharides, disaccharides, and disaccharide alcohols were confirmed under conditions of increased gelling aid contents. Only when either a non-reducing disaccharide, such as trehalose or sucrose; or a non-reducing disaccharide alcohol, such as maltitol, lactitol, or isomalt, was added, no deposition of potassium chloride was observed even after 1 week. When other carbohydrates were added to the film in the same amount as that of the non-reducing disaccharide or non-reducing disaccharide alcohol, the saccharides other than non-reducing disaccharides and non-reducing disaccharide alcohols did not inhibit deposition of the gelling aid. When lactose was added in Comparative Example 3, as shown in Table 2, transparency was lost.

Even when sodium chloride was used as a gelling aid, the addition of trehalose similarly inhibited deposition of sodium chloride. These results suggest that non-reducing disaccharides and non-reducing disaccharide alcohols are effective for inhibiting the deposition of gelling aids.

Furthermore, when a non-reducing disaccharide or a non-reducing disaccharide alcohol was added, almost no reduction in film hardness was observed. In contrast, when xylitol or erythritol, which are monosaccharide sugar alcohols, was added, a slight reduction in film hardness was observed. These results suggest that non-reducing disaccharides and non-reducing disaccharide alcohols are also effective for inhibiting deposition of a gelling aid, while maintaining appropriate hardness of a hard capsule.

The invention claimed is:

1. A hard capsule comprising
a film containing
    (1) a cellulose compound,
    (2) a gelling agent,
    (3) a gelling aid, and
    (4) at least one member selected from the group consisting of a non-reducing disaccharide and a non-reducing disaccharide alcohol,
wherein:
the cellulose compound is hydroxypropylmethylcellulose,
the gelling agent is kappa-carrageenan,
the gelling aid is potassium chloride or sodium chloride,
the at least one member selected from the group consisting of a non-reducing disaccharide and a non-reducing disaccharide alcohol is trehalose, sucrose, maltitol, lactitol and/or isomalt, and
the film comprises 0.05 to 8 mass % of the gelling agent, 0.65 to 0.8 mass % of the gelling aid, and 3 to 8 mass % of the at least one member selected from the group consisting of a non-reducing disaccharide and a non-reducing disaccharide alcohol, based on 100 mass % of the total film components of the hard capsule, excluding moisture.

2. The hard capsule according to claim 1, further comprising a plasticizer and/or a light-shielding agent.

3. A hard capsule-preparing solution containing
    (1) a cellulose compound,
    (2) a gelling agent,
    (3) a gelling aid,
    (4) at least one member selected from the group consisting of a non-reducing disaccharide and a non-reducing disaccharide alcohol, and
    (5) a solvent,
wherein:
the cellulose compound is hydroxypropylmethylcellulose,
the gelling agent is kappa-carrageenan,
the gelling aid is potassium chloride or sodium chloride,
the at least one member selected from the group consisting of a non-reducing disaccharide and a non-reducing disaccharide alcohol is trehalose, sucrose, maltitol, lactitol and/or isomalt, and
the solution contains 0.05 to 8 mass % of the gelling agent, 0.65 to 0.8 mass % of the gelling aid, and 3 to 8 mass % of the at least one member selected from the group consisting of a non-reducing disaccharide and a non-reducing disaccharide alcohol, based on 100 mass % of the total components, excluding the solvent.

4. The hard capsule-preparing solution according to claim 3, further comprising a plasticizer and/or a light-shielding agent.

5. A method for preparing a hard capsule comprising the step of preparing a hard capsule using the hard capsule-preparing solution according to claim 3.

6. The method for preparing a hard capsule according to claim 5, wherein the method is a cold gelation method.

* * * * *